(12) United States Patent
Nelson

(10) Patent No.: US 9,021,860 B2
(45) Date of Patent: May 5, 2015

(54) MOBILE SCENT TESTER

(75) Inventor: Patti Lynn Nelson, Forked River, NJ (US)

(73) Assignee: Q Research Solutions, Inc., Old Bridge, NJ (US)

( * ) Notice: Subject to any disclaimer, the term of this patent is extended or adjusted under 35 U.S.C. 154(b) by 374 days.

(21) Appl. No.: 13/386,000

(22) Filed: Mar. 20, 2012

(65) Prior Publication Data

US 2012/0247182 A1 Oct. 4, 2012

Related U.S. Application Data

(60) Provisional application No. 61/516,065, filed on Mar. 29, 2011.

(51) Int. Cl.
*G01N 33/00* (2006.01)
*G01N 1/22* (2006.01)

(52) U.S. Cl.
CPC ........ *G01N 33/0001* (2013.01); *G01N 33/0009* (2013.01); *G01N 1/22* (2013.01)

(58) Field of Classification Search
CPC .. G01N 1/22; G01N 33/0009; G01N 33/0021
See application file for complete search history.

(56) References Cited

U.S. PATENT DOCUMENTS

| | | | |
|---|---|---|---|
| 6,511,852 B1 * | 1/2003 | Ledig | 436/181 |
| 7,419,535 B2 * | 9/2008 | Malle | 96/222 |
| 2001/0011473 A1 * | 8/2001 | Marshall et al. | 73/23.34 |
| 2008/0283626 A1 * | 11/2008 | Aldana et al. | 239/68 |
| 2009/0320559 A1 * | 12/2009 | Lemieuvre et al. | 73/23.34 |
| 2010/0176950 A1 * | 7/2010 | Bartholf et al. | 340/572.7 |

\* cited by examiner

*Primary Examiner* — Paul West
(74) *Attorney, Agent, or Firm* — Lerner, David, Littenberg, Krumholz & Mentlik, LLP

(57) ABSTRACT

A self-contained mobile apparatus which replicates the evaluation of scents, fragrances, aromas and odors in controlled and home environments. The apparatus simulates various stages of the consumer experience and has adjustable settings for dosing, air flow, and room size. The scented compound sample is placed within a cabinet having an enclosed sample chamber which is connected to an upward facing sample tube. An air fan is mounted within the sample chamber which circulates and controls sample air flow upward to a testing station wherein the sample air flow is tested for the identification and the concentration of the scent contained therein. A return air chamber and filter are mounted below the testing station. The filtered return air is controlled downward by a return air blower to provide an exhaust out through the bottom of the apparatus.

24 Claims, 2 Drawing Sheets

SECTION A-A'

SECTION B-B'

MOBILE SCENT TESTER

CROSS-REFERENCE TO RELATED APPLICATIONS

The present application claims the benefit of the filing date of U.S. Provisional Application No. 61/516,065, filed Mar. 29, 2011.

FIELD OF THE INVENTION

The present invention relates to an apparatus for use in the testing of individual compound test samples for identification, concentration and consumer appeal of the scent contained therein. The present invention can be used to analyze scents, fragrances, aromas and odors in controlled and home environments. The scent tester is mounted on casters so that it can be easily transported to different indoor and outdoor locations.

SUMMARY OF THE INVENTION

Scented compounds are common within nature, the consumer, the commercial and the industrial markets. It is essential that scented compounds be tested so as to identify the scent; its character, profile, intensity and strength. It is necessary that the scent be tested so that it can be modified to be more pleasing to the user when it is contained within consumer products such as perfumes, air fresheners, candles, colognes, shampoos, lotions, soaps, detergents, cosmetics, paints, insecticides, etc. Heretofore, scent testing has been conducted by relying upon a tester, either an individual or a group of panelists, entering an expensive, thoroughly cleaned and sealed test room to subjectively smell a single test sample such as a candle, aerosol, cream, or powder in a container such as a beaker, bottle, or box, etc. The prior practice testing was not objective or scientific because it depended solely upon the subjective smelling of a scented sample compound by the tester. The present invention has a broader scope adding to the prior practice.

A disadvantage of the prior practice was that the air flows to and from the test sample were not precisely controlled within the test room. Thus there were not uniform test, conditions which could adversely affect the test results. The present invention eliminates such adverse potential in that the air flows are precisely and uniformly set for each test sample which provides scientific reliability of the test results. A further disadvantage of the prior practice was that the expensive test room was limited to the testing of a single test compound sample at one time, because the test room had to be thoroughly cleaned in a time-consuming and expensive procedure after each sample was tested and before a different sample could be tested. This involved the possibility of contamination from remnants of the previous sample. The present invention effectively eliminates the possibility of cross contamination because the air flows from each sample are completely contained, isolated and effectively filtered before those air flows are exhausted into the test room. This permits multiple apparatus and testing of different samples to be operated at the same time within a test room.

The present invention provides an apparatus using standardized test samples, adjustable and controlled air flows under uniform testing conditions to make the testing more objective and scientific, while, at the same time, reducing testing costs by the ability to use the apparatus in different and more convenient locations.

An aspect of the present disclosure relates to a scent testing device. The scent testing device includes a housing defining an interior and an exterior. The exterior of the housing has a testing location with a source opening between the interior and exterior and a return opening between the interior and exterior. A sample test chamber is disposed within the interior of the housing. The sample test chamber is selectively openable to the exterior of the housing and closeable so as to be sealed within the interior of the housing. The sample test chamber is further in fluid communication with the source opening. A first airflow device is positioned within the interior of the housing and is in communication with the sample test chamber and operable to direct a sample air flow from the sample test chamber and out of the source opening to the exterior of the device. A second airflow device is within the interior of the housing and is in communication with the return opening and operable to draw the sample air flow from the exterior of the device through the return opening.

The first airflow device can be a blower positioned between the sample test chamber and the source opening. The scent testing device can further include a source conduit between the sample test chamber and the source opening to facilitate the fluid communication between the sample test chamber and the source opening, and the blower can be positioned within the source conduit. The scent testing device can further include a lid positioned adjacent the source opening that is operable to selectively cover and uncover the source opening.

The housing can include a sample chamber door that is closeable against adjacent portions of the housing to facilitate the selective closing of the sample test chamber within the interior of the housing with the sample chamber door being at least partially removable to facilitate the selective opening of the sample test chamber to the exterior of the housing. The sample chamber door can include one or more electronic devices removably attached therewith and positionable within the sample test chamber when the sample chamber door is sealed against the adjacent portions of the housing. The one or more electronic devices can be electrically connected with a power source on the exterior of the housing. The scent testing device can further include a secondary cover mounted on the exterior of the housing that is operable to selectively obscure the sample chamber door.

The scent testing device can further include a filter disposed within the interior of the housing that is in fluid communication with the return opening. In such an example, the second airflow device can be further operable to direct the sample airflow through the filter after drawing the sample airflow from the exterior of the device through the return opening. Such a scent testing device can further include a return air chamber disposed within the interior of the housing opposite the testing location that is in fluid communication with the return opening, the filter being disposed within the return air chamber. The return opening can be one of a plurality of return openings between the interior and the exterior of the housing within the test area. The scent testing device can further include an exhaust outlet open between the interior and exterior of the housing. In such an example, the filter can be in fluid communication with the exhaust outlet and can be positioned between the return opening and the exhaust outlet.

In an example of the scent testing device, the first airflow device and the second airflow device can be adjustable to control respective flow rates of the sample air flow out of the source opening and into the return opening. The respective flow rates of the sample air flow out of the source opening and into the return opening can be controlled so as to maintain the sample air flow within a predetermined area adjacent the testing location.

The testing location can be defined within a recess in first surface of the exterior of the housing. In a further example, the scent testing device can further include a bloom guard surrounding a portion of the testing location and extending away from the housing along the portion of the testing location.

Another aspect of the present disclosure relates to a method for producing a scented test airflow within a predetermined area. The method includes creating a first pressure differential between a test chamber within an interior of a testing unit and an exterior of the testing unit. The test chamber is in fluid communication with the exterior of the testing unit via a source opening in the testing unit, and a scent sample is positioned within the test chamber. The method also includes allowing the first pressure differential to cause a source flow of air containing scent particles from the scent sample to flow out from the source opening. A second pressure differential is created between a return conduit within the testing unit and the exterior of the testing unit. The return conduit is isolated from the test chamber and is in fluid communication with the exterior of the testing unit via a return opening adjacent the source opening. The method also includes controlling the first pressure differential and the second pressure differential such that a return air flow containing at least a portion of the scent particles from the source flow are drawn through the return opening and back into the testing unit.

The method can further include removing the scent particles from the return flow after return air flow containing at least a portion of the scent particles from the source flow are drawn through the return opening and back into the testing unit and subsequently exhausting air from the return flow out from the testing unit at a location on the exterior of the testing unit spaced apart from the source opening.

In an example, the scented test airflow can be a first scented test airflow, and the method can further include producing a second scented test airflow by the same steps and in the same room in which the first scented test airflow is produced.

In another example, the first pressure differential can be controlled such that the sample flow is at a rate between 0 and 3 cubic feet per minute, and the second pressure differential can be controlled such that the return flow is at a rate of between 0 and 70 cubic feet per minute, the rate of the return air flow being greater than the rate of the sample air flow. The control of the rate of the sample air flow and the rate of the return air flow can include manual adjustments thereto.

These and other objects and advantages of the present invention will become apparent to those skilled in the art and from the following drawings and descriptions.

BRIEF DESCRIPTION OF THE DRAWINGS

The mobile scent tester of the present invention is depicted in the following drawings which form a part of this disclosure, and wherein.

DETAILED DESCRIPTION

Figure 1:
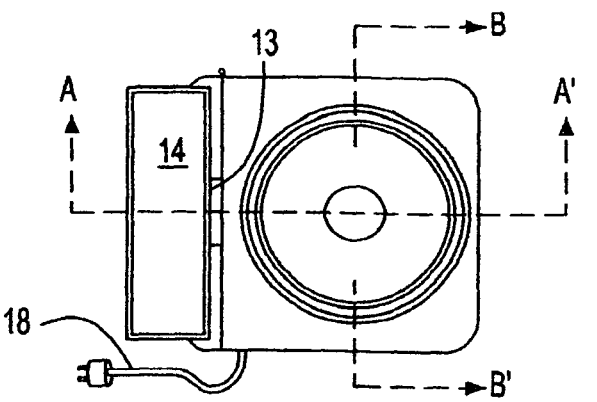
FIG. 1 is a plan view of the mobile scent tester of the present invention.
Figure 3:
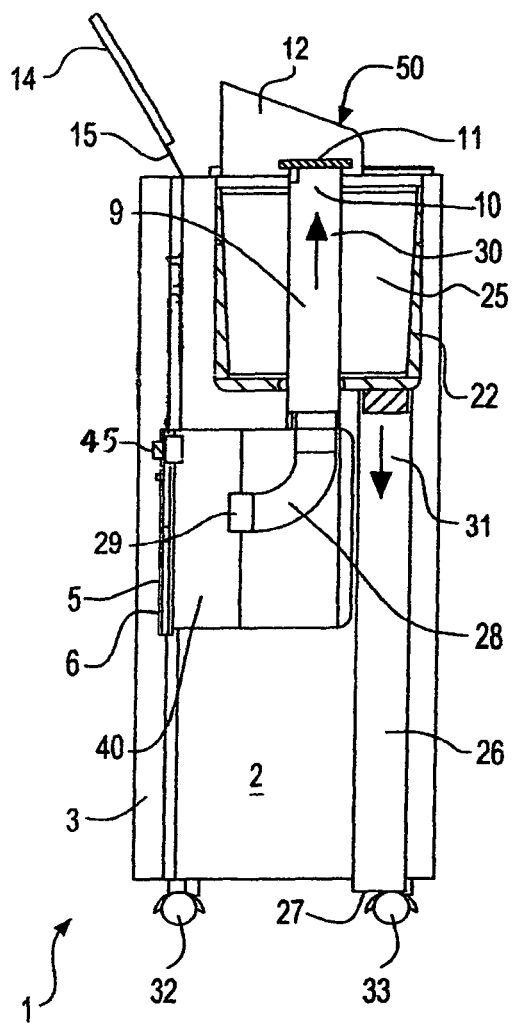
FIG. 3 is a side sectional view of the mobile scent tester along line A-A' of FIG. 1.
Figure 4:
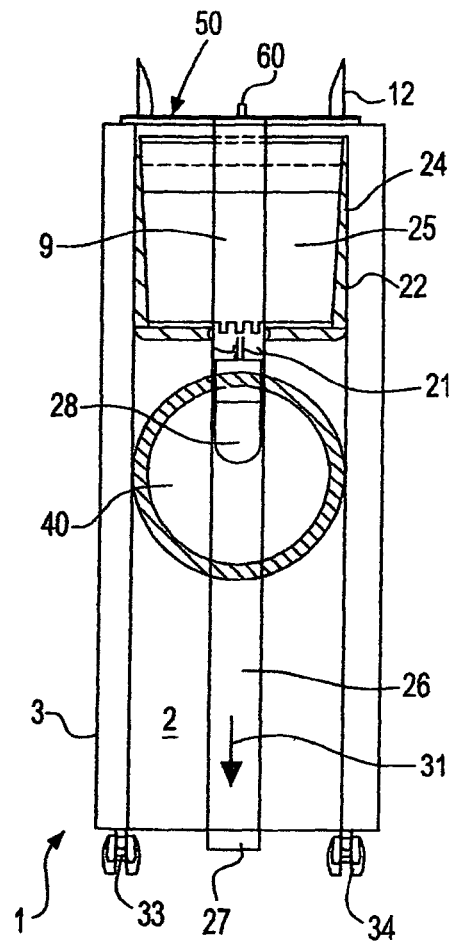
FIG. 4 is a front sectional view of the mobile scent tester along line B-B' of FIG. 1.
Figure 2:
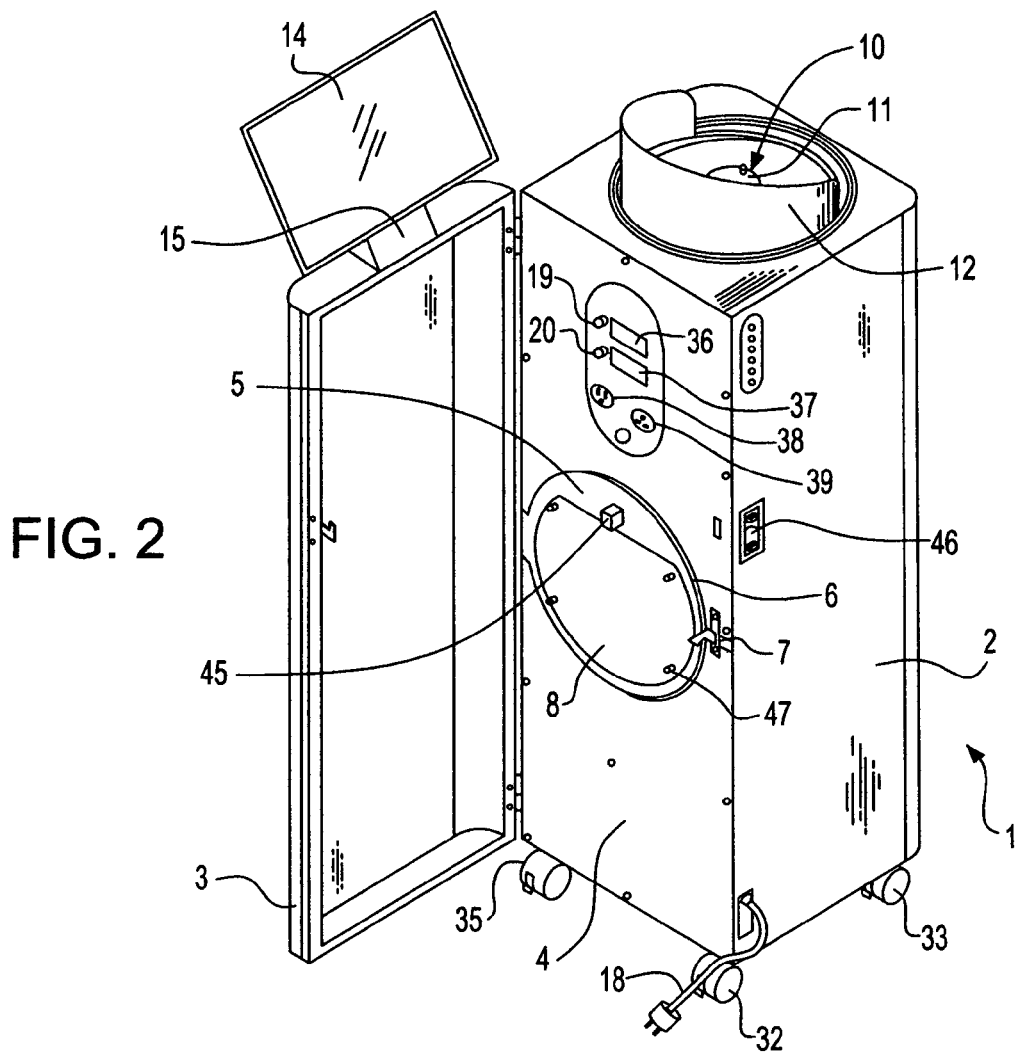
FIG. 2 is a front perspective view of the mobile scent tester with the cabinet door open.
Figure 5:
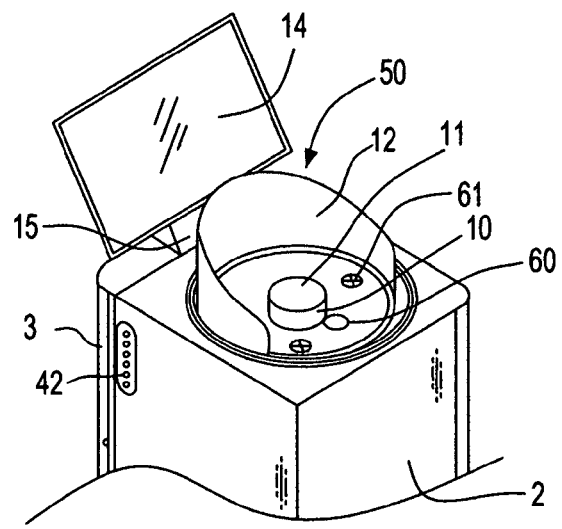
FIG. 5 is a rear perspective view of the top of the scent tester of the present invention.

Referring to the above drawings by numerals and letters of reference, the preferred embodiment of the mobile scent tester of the present invention is generally shown as 1. The scent tester 1 is fabricated of non-absorbing stainless steel in the form of a cabinet 2 which has a rectangular front door 3. After twisting the door lock 45 which unlocks the cabinet front door 3, there is shown a rectangular security shield 4 to protect the operating mechanisms within the cabinet 2. At the center front portion of the security shield 4 is a circular, side-hinged sample chamber door 5 which, when closed, is tightly air-sealed with a peripheral gasket 6 and by a sample chamber door lock 7. The sample chamber door 5 also has bolts 47 therein further securing a generally circular door insert 8 to which may be internally attached a variety of electric modular units for conducting test applications according to protocols developed for a specific sample. After unbolting and placing the circular insert 8 which is relevant to the application in question, the tester places a standardized test sample through the sample chamber door 5 opening into a cylindrical sample test chamber 40. The sample chamber door 5 is then closed. An upwardly extending air sample tube 9 is connected at its lower end to the top of the sample test chamber 40. The air sample tube 9 exits at its upper end to a sample tube air exit 10 passing through to a testing station, generally designated as 50, at the top of the cabinet 2. The sample tube air exit 10 is normally closed by a swivel cover 11. A sample air fan 45 is mounted within the sample chamber 40 to circulate sample air flow 30 in the range of 0-3 cubic feet per minute ("cfm"), and in an example 2.0 cfm, upward from within the sample test chamber 40. Such air then travels through the air sample tube 9 and, upon opening of the swivel cover 11, out through the sample air exit 10 to the testing station 50 at the top of the cabinet 2 and outward to the testing station 50 at the top of the cabinet 2. The sample air flow 30 provides positive air flow at the sample air exit 10, which is partially enclosed within a bloom guard 12 in the form of a partial semi-circular ring around the sample tube air exit 10. The bloom guard 12 can have a shape such that it is higher in the area away from the tester at the front of the cabinet 2 and tapering down towards the rear of the cabinet 2, within the area directly in front of the tester. The bloom guard 12 can have a height of about 5.5 inches at the front, tapering down at 20 degrees to about 2.25 inches at each end in the rear. The open area in the rear can be about 130 degrees. The bloom guard 12 helps to minimize the loss of sample air flow 30 into the test area while maximizing the ease of he tester analyzing the sample air flow 30. The sample air flow 30 is then smell-tested by the tester who is recruited with a highly developed natural olfactory talent augmented by extensive training, or by a panel of average consumer tester.

In addition, the mobile scent tester of the present invention can be adapted for more scientific testing by connecting the testing station 50 to test instruments such as spectrophotometer, pH meter, electronic sensors, etc. The scientific testing equipment can be connected to electric receptacles 38 and 39 mounted on a side of the cabinet 2 from power cord 18. After the sample air flow 30 has been tested, return air flow 31 is sucked from the testing station 50 and is moved downward through return air inlet perforations 61 within the testing station 50 into a return air chamber 22 mounted below the testing station 50. The return air chamber 22 encloses a filter cartridge 24 with activated carbon pellets 25 therein, which can be about 4 mm size. Thence, the filtered return air flow 31 is moved downward at a range of about 0-70 cfm (e.g., 40 cfm) by a return air blower 21 mounted within a return air tube 26 attached at the bottom of the return air chamber 22, and thence out through a return air exhaust 27 at the bottom of the cabinet 2. The return air flow 31 is effectively filtered or scrubbed of all of the scent therein. The return air flow 31 is exhausted out into the location of the scent tester 1 without changing the quality of the air at the testing station 50 or adversely influencing the tests thereon. This permits the simultaneous operation of multiple units of the present invention at the same time, on different samples, in a test room. The sample air flow 30 can be precisely controlled within a range of 0-3 cfm (e.g., 2.0 cfm) and the return air flow 31 can also be precisely controlled within a range of 0-70 cfm (e.g., 40 cfm) by monitoring the speed indicators 19,20 and by adjusting the speeds of the sample air fan 45 and the return air blower 21, with the fan speed adjustment knobs 36, 37 mounted on a side of the cabinet 2. In addition a velocimeter 60 may be mounted at the rear of the testing station 50 to further monitor the sample air flow 30 within the desired range.

Additionally, the mobile scent tester 1 can be provided with lockable casters 32,33,34 and 35 at the corners on the bottom of the cabinet 2 so that the cabinet 2 can be easily transported within the test room or different test locations.

The scent tester 1 can be further provided with a removable small sample chamber 28 in the form of a tubular elbow which has an air opening 29 at its lower end within the sample test chamber 40. The upper end of the small sample chamber 23 can be removeably attached to the bottom of the sample air tube 9. This can allow the scent tester 1 to be used for smaller and non-standard test samples.

The use of the scent tester apparatus 1 of the present invention enables the tester to more objectively and scientifically test for identity and concentration of scents than with the prior practice.

The circulation of the sample air flow 30 and the return air flow 31 are tightly controlled by the speeds of the sample air fan 45 and the return air blower 21 so that positive pressure at the sample tube air exit 10 is uniform which assists the operator to make more accurate objective and scientific tests of the standardized test samples. The test information can then be used to confidently confirm or modify the test sample scent for commercial, industrial and consumer use.

The scent tester 1 is fabricated of non-absorbing materials (e.g., stainless steel) but other non-polluting and non-dissolving materials may also be used, such as porcelain coated, metal, ceramic, plastic, etc.

Method of Operation

The supplier of the mobile scent tester 1 has developed detailed protocols for testing, operation, maintenance and cleaning. The material protocols require that the mobile scent tester 1 be operated within a clean environment to avoid contamination by other scents. Additionally, the scent tester 1 will preferably be thoroughly maintained for optimum operation. All moving parts would preferably be lubricated with non-smelling materials, which can be accomplished by using a clean cloth wet with distilled water and isopropyl alcohol on all surfaces.

For optimum operation, the scented compound samples can be prepared in standardized sizes and containers in accordance with the protocols. The tester would preferably be certified by the supplier in its operation based on various protocols and instructions.

The tester can place the compound scent sample of the standardized amount directly or within the standardized container. The standardized sample and container can, thus, be placed within the applicable test chamber 28, 40, which is then air sealed by closing the sample chamber door 5. The tester can then turn on the sample air fan 45 and the return air blower 21 and smell-test the sample air flow 30 at the inspection station 50. The tester compares his smell tests with his experience and with reference samples of other sample scented compounds, which can be provided by the supplier. Additional smell-tests can be made with the speeds of the sample air fan 45 and the return fan blower 21 being adjusted by the speed adjustment knobs 36,37 so that the positive sample air flow 30 at the inspection station is about about 2.0 cfm, for example.

The operation of the scent tester 1 can be monitored by function indicator lights 42 mounted on a side of the scent tester 1. The operation of the scent tester 1 can be further monitored by the tester using a video screen and camera 14 mounted on a bracket 15 attached to the front top of the cabinet 2 in order to display concepts, facial expressions of the tester, commercials, etc. and to provide direct data entry capability.

Additional monitoring of the sample air flow 30 and the return air flow 31 can be accomplished by the operator monitoring fan speed indicator lights 36, 37 for use with fan speed adjustment knobs 19, 20.

The mobile scent tester of the present invention has been defined by the above disclosure, but it should be understood that this is by way of illustration only and that the present invention is not necessarily limited thereto. Modifications and variations will be apparent as those skilled in the art will readily understand. Accordingly, such modifications and variations of the disclosed present invention are considered to be within the purview and scope of the disclosure and the following claims:

I claim:

1. A scent testing device, comprising:
   a housing defining an interior and an exterior, the exterior of the housing having a testing location that includes a source opening between the interior and exterior;
   a sample test chamber within the interior of the housing, an interior of the sample test chamber being selectively openable to the exterior of the housing and closeable so as to be sealed within the interior of the housing, wherein the sample test chamber is openable and closeable while in fluid communication with the source opening, and is sized to accept a variety of different scent samples and scented product forms;
   a first gas flow device in communication with the sample test chamber and operable to direct a sample gas flow from the sample test chamber and out of the source opening to an exterior of the device;
   a return opening between the interior and exterior of the housing; and
   a second gas flow device in communication with the return opening and operable to draw the sample air flow from the exterior of the device through the return opening.

2. The scent testing device of claim 1, wherein the first gas flow device is a blower positioned between the sample test chamber and the source opening.

3. The scent testing device of claim 2, further including a source conduit between the sample test chamber and the source opening to facilitate the fluid communication between the sample test chamber and the source opening, the blower being positioned within the source conduit.

4. The scent testing device of claim 1, further including a lid positioned adjacent the source opening and operable to selectively cover and uncover the source opening.

5. The scent testing device of claim 1, wherein the housing includes a sample chamber door that is closeable against adjacent portions of the housing to facilitate the selective closing of the sample test chamber within the interior of the housing, the sample chamber door being at least partially removable to facilitate the selective opening of the sample test chamber to the exterior of the housing.

6. The scent testing device of claim 5, further including a secondary cover mounted on the exterior of the housing and operable to selectively obscure the sample chamber door.

7. The scent testing device of claim 1, wherein the housing includes a power source.

8. The scent testing device of claim 1, further including a filter disposed within the interior of the housing and in fluid communication with the return opening, and wherein the second gas flow device is further operable to direct the sample gas flow through the filter after drawing the sample gas flow from the exterior of the device through the return opening.

9. The scent testing device of claim 8, further including a return gas chamber disposed within the interior of the housing opposite the testing location and in fluid communication with the return opening, the filter being disposed within the return gas chamber.

10. The scent testing device of claim 9, wherein the return opening is one of a plurality of return openings between the interior and the exterior of the housing within the test area.

11. The scent testing device of claim 8, further including an exhaust outlet open between the interior and exterior of the housing, the filter being in fluid communication with the exhaust outlet and being positioned between the return opening and the exhaust outlet.

12. The scent testing device of claim 1, wherein the first gas flow device and the second gas flow device are adjustable to control respective flow rates of the sample gas flow out of the source opening and into the return opening.

13. The scent testing device of claim 12, wherein the respective flow rates of the sample gas flow out of the source opening and into the return opening can be controlled so as to maintain the sample gas flow within a predetermined area adjacent the testing location.

14. The scent testing device of claim 1, wherein the testing location is defined within a recess in a first surface of the exterior of the housing.

15. The scent testing device of claim 1, further including a bloom guard surrounding a portion of the testing location and extending away from the housing along the portion of the testing location.

16. A method for producing a scented test gas flow within a predetermined testing area, comprising:
generating and allowing a first gas flow to pass through a test chamber within an interior of a testing unit, the test chamber being in fluid communication with an exterior of the testing unit via a source opening in the testing unit, a scent sample being positioned within the test chamber;
allowing the first gas flow to cause a source gas flow containing scent particles from the scent sample to flow out of the source opening for testing by a user at the testing area; and
generating a second gas flow through a return conduit within the testing unit, the return conduit being isolated from the test chamber and being in fluid communication with the exterior of the testing unit via a return opening adjacent the source opening; and
controlling the first and second gas flows such that a return gas flow containing at least a portion of the scent particles from the source gas flow effective to avoid adversely influencing the quality of air at the testing area is drawn through the return opening and back into the testing unit.

17. The method of claim 16, further including:
removing the scent particles from the return gas flow after the return gas flow containing at least a portion of the scent particles from the source gas flow are drawn through the return opening and back into the testing unit; and
subsequently exhausting gas from the return gas flow out of the testing unit at a location on the exterior of the testing unit spaced apart from the source opening.

18. The method of claim 17, wherein the scented test gas flow is a first scented test gas flow, the method further including producing a second scented test gas flow by the same steps and in the same location in which the first scented test gas flow is produced.

19. The method of claim 16, wherein the first gas flow is controlled such that the source gas flow is at a rate between 0 and 3 cubic feet per minute, and wherein the second gas flow is controlled such that the return gas flow is at a rate of between 0 and 70 cubic feet per minute, the rate of the return gas flow being greater than the rate of the source gas flow.

20. The method of claim 19, wherein the rate of the source gas flow and the rate of the return gas flow are manually adjustable.

21. A scent testing device, comprising:
a housing defining an interior and an exterior, the exterior of the housing having a testing location that includes a source opening between the interior and exterior, the scent testing device being portable from a first location to a second remote location;
a sample test chamber within the interior of the housing that is in fluid communication with the source opening, an interior of the sample test chamber being selectively openable to the exterior of the housing and closeable so as to be sealed within the interior of the housing, wherein the sample test chamber is openable and closeable while in fluid communication with the source opening;
a first gas flow device in communication with the sample test chamber and operable to direct a sample gas flow from the sample test chamber and out of the source opening to the exterior of the device for testing a scent sample housed in the sample test chamber;
a return opening between the interior and exterior; and
a second gas flow device in communication with the return opening and operable to draw the sample gas flow from the exterior of the device through the return opening.

22. The scent testing device of claim 21, further comprising a bloom guard surrounding a portion of the testing location and extending away from the housing along the portion of the testing location.

23. The scent testing device of claim 21, wherein respective flow rates of the sample gas flow out of the source opening and into the return opening can be controlled so as to maintain the sample gas flow within a predetermined area adjacent the testing location.

24. A method of using the scent testing device of claim 21 comprising:
providing the scent testing device of claim 21;
actuating the first gas flow device to cause a first gas flow to pass through the test chamber and interact with the scent sample; and
releasing the first gas flow, at least partially infused with scent particles from the scent sample, out of the source opening for testing by the user.

* * * * *